US008652240B2

(12) United States Patent
Sugiyama et al.

(10) Patent No.: US 8,652,240 B2
(45) Date of Patent: Feb. 18, 2014

(54) FINE PARTICLE SENSOR AND MOUNTING STRUCTURE THEREFOR

(75) Inventors: Takeshi Sugiyama, Fuwa-gun (JP); Masayuki Motomura, Komaki (JP); Toshiya Matsuoka, Kaizu (JP); Keisuke Tashima, Kasugai (JP); Hitoshi Yokoi, Ama (JP)

(73) Assignee: NGK Spark Plug Co., Ltd., Aichi (JP)

( * ) Notice: Subject to any disclaimer, the term of this patent is extended or adjusted under 35 U.S.C. 154(b) by 146 days.

(21) Appl. No.: 13/422,379

(22) Filed: Mar. 16, 2012

(65) Prior Publication Data

US 2012/0234172 A1    Sep. 20, 2012

(30) Foreign Application Priority Data

Mar. 17, 2011 (JP) ................................ 2011-058627

(51) Int. Cl.
*B03C 3/34* (2006.01)
(52) U.S. Cl.
USPC ............... 96/19; 60/275; 60/311; 73/28.02; 73/114.71; 73/863.23; 95/3; 96/26
(58) Field of Classification Search
USPC ......... 96/19, 26, 62, 63, 95; 95/3, 78; 60/275, 60/311; 73/28.02, 114.71, 863.23
See application file for complete search history.

(56) References Cited

U.S. PATENT DOCUMENTS

| | | | | |
|---|---|---|---|---|
| 3,472,067 A | * | 10/1969 | Chew | 73/863.58 |
| 3,473,118 A | * | 10/1969 | Tassicker et al. | 324/722 |
| 4,534,213 A | * | 8/1985 | Mirikidani | 73/114.71 |
| 5,117,680 A | * | 6/1992 | Colvin | 73/114.71 |
| 7,406,855 B2 | | 8/2008 | Tikkanen et al. | |
| 7,650,780 B2 | * | 1/2010 | Hall | 73/114.71 |
| 7,707,875 B2 | * | 5/2010 | Lee | 73/114.71 |
| 8,225,648 B2 | * | 7/2012 | Nelson | 73/114.71 |
| 8,310,249 B2 | * | 11/2012 | Paterson | 324/693 |
| 2005/0160840 A1 | | 7/2005 | Allmendinger | |
| 2008/0072756 A1 | * | 3/2008 | Lee | 96/19 |
| 2011/0050243 A1 | | 3/2011 | Tikkanen | |
| 2011/0132342 A1 | * | 6/2011 | Soltis et al. | 123/703 |

FOREIGN PATENT DOCUMENTS

| | | | | |
|---|---|---|---|---|
| DE | 102008000372 A1 | | 8/2009 | |
| GB | 2450605 A | | 12/2008 | |
| JP | 6-292839 A | * | 10/1994 | 96/19 |
| JP | 2007-514923 A | | 6/2007 | |
| WO | 2004113904 A1 | | 12/2004 | |
| WO | 2009109688 A1 | | 9/2009 | |
| WO | WO 2009/109688 A1 | | 9/2009 | |
| WO | 2011104426 A1 | | 9/2011 | |

\* cited by examiner

*Primary Examiner* — Richard L Chiesa
(74) *Attorney, Agent, or Firm* — Sughrue Mion, PLLC

(57) ABSTRACT

There is provided a fine particle sensor for detecting fine particles in exhaust gas, including an ion generating unit for generating ions by corona discharge, a charging unit for charging the fine particles by some of the generated ions, an ion trapping unit for trapping a remainder of the generated ions and a casing for accommodating therein the charging unit and the ion trapping unit in a given arrangement direction. The casing has a gas inlet hole and a gas outlet hole formed in a circumferential wall thereof so that the exhaust gas flows in the charging unit through the gas inlet hole and flows out of the ion trapping unit through the gas outlet hole. The gas inlet hole and the gas outlet hole are arranged in such a manner as to at least partially overlap each other when viewed in the given arrangement direction.

5 Claims, 8 Drawing Sheets

FIG.8A FIG.8B
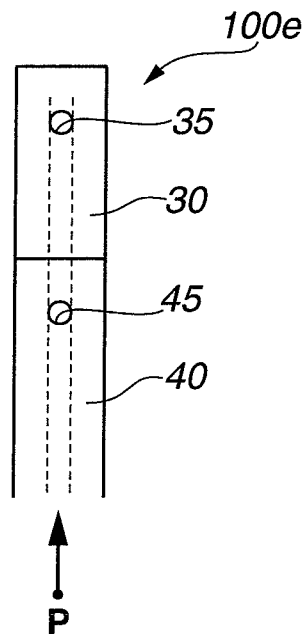
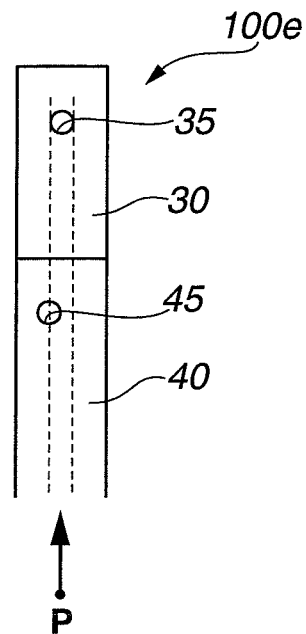
FIG.8C
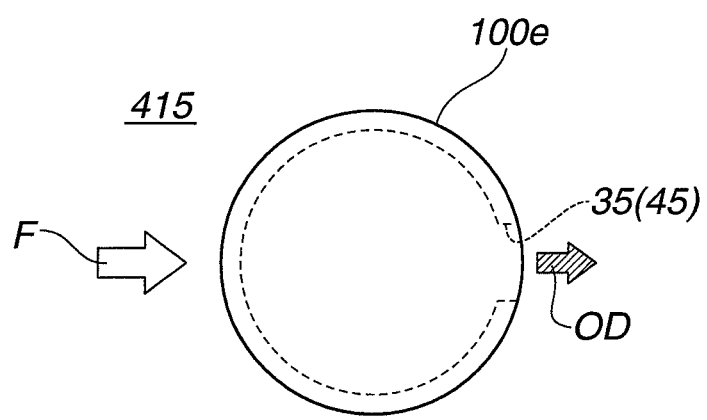

FINE PARTICLE SENSOR AND MOUNTING STRUCTURE THEREFOR

BACKGROUND OF THE INVENTION

The present invention relates to a fine particle sensor for detecting fine particles (e.g. soot) in exhaust gas and a mounting structure for mounting a fine particle sensor to an exhaust pipe of an internal combustion engine.

In the following description, the terms "front" and "rear" are used with respect to the axial direction of a fine particle sensor and, more specifically, the direction of insertion of the fine particle sensor into an exhaust pipe; and the terms "upstream" and "downstream" are used with reference to the direction of gas flow in the fine particle sensor or in the exhaust pipe.

Fine particles (e.g. soot) are contained in exhaust gases of internal combustion engines (such as diesel engines and gasoline engines). It is thus common practice to mount a fine particle sensor on an exhaust pipe of the internal combustion engine in order to detect the amount of fine particles in the exhaust gas and limit the amount of fine particles discharged to the atmosphere as disclosed in Japanese Translation of PCT International Application Publication No. JP-T-2007-514923 and PCT International Application Publication No. WO2009/109688. However, there is a problem that the detection accuracy of the conventional fine particle sensor tends to vary depending on the flow of the exhaust gas in the exhaust pipe.

SUMMARY OF THE INVENTION

It is therefore an object of the present invention to provide a technique for improving the accuracy of detection of fine particles in exhaust gas flowing through an exhaust pipe of an internal combustion engine.

According to one aspect of the present invention, there is provided a fine particle sensor for detecting fine particles in exhaust gas flowing through an exhaust pipe of an internal combustion engine, comprising: an ion generating unit that generates ions by corona discharge; a charging unit that charges, with some of the ions generated by the ion generating ions, the fine particles in the exhaust gas emitted from the internal combustion engine through the exhaust pipe; an ion trapping unit that traps a remainder of the ions generated by the ion generating unit, which remain as excess ions without being used for charging of the fine particles in the charging unit, so that the fine particle sensor can generate an output signal responsive to the amount of the fine particles in the exhaust gas according to the amount of the excess ions trapped by the ion trapping unit; and a casing inserted inside the exhaust pipe and accommodating therein the charging unit and the ion trapping unit adjacent to each other in a given arrangement direction, the casing having, formed in a circumferential wall thereof, a gas inlet hole for introducing the exhaust gas from the exhaust pipe into the charging unit and a gas outlet hole for discharging the exhaust gas that includes the fine particles charged with the some of the ions generated by the ion generating unit, out from the ion trapping unit to the exhaust pipe, wherein the gas inlet and outlet holes are arranged in such a manner as to at least partially overlap each other when the fine particle sensor is viewed in the given arrangement direction.

According to another aspect of the present invention, there is provided a mounting structure for mounting the above fine particle sensor to an exhaust pipe of an internal combustion engine, wherein the fine particle sensor is arranged in such a manner that openings of the gas inlet and outlet holes are directed downstream of the flow of exhaust gas in the exhaust pipe.

The other objects and features of the present invention will also become understood from the following description.

BRIEF DESCRIPTION OF THE DRAWINGS

FIGS. 8A and 8B are schematic views showing the arrangement of exhaust gas inlet and outlet holes in the fine particle sensor according to the exemplary embodiment of the present invention.

FIG. 8C is a schematic view showing a mounting structure for mounting the fine particle sensor to an exhaust pipe according to the exemplary embodiment of the present invention.

DESCRIPTION OF THE EMBODIMENTS

The present invention will be described below with reference to the drawings.

Figure 1A:
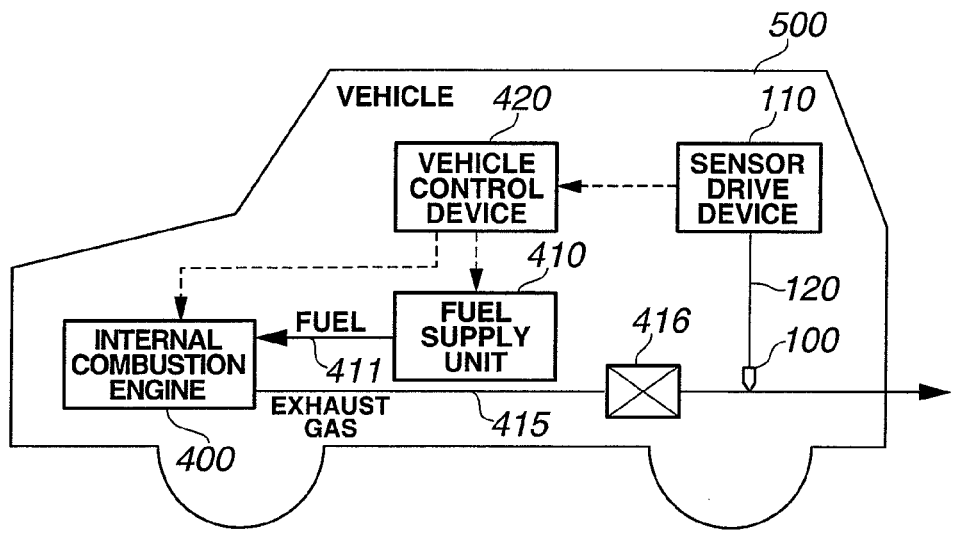
FIGS. 1A and 1B are schematic views of an automotive vehicle equipped with a fine particle sensor according to one exemplary embodiment of the present invention.

As shown in FIG. 1A, there is provided according to one embodiment of the present invention an automotive vehicle 500 that includes an internal combustion engine 400, a fuel supply unit 410, a filter unit 416, a vehicle control device 420 and a fine particle detection system with a fine particle sensor 100, a cable 120 and a sensor drive device 110.

The internal combustion engine 400 is, for example, a diesel engine as a power source of the vehicle 500 and equipped with an exhaust pipe 415 to emit therethrough exhaust gas to the outside of the vehicle 500.

The fuel supply unit 410 is adapted to supply fuel into the internal combustion engine 400 through a fuel pipe 411.

The filter unit 416 is, for example, a diesel particulate filter (DPF) and is attached to the exhaust pipe 415 of the internal combustion engine 400 so as to remove fine particles (e.g soot) from the exhaust gas.

The vehicle control device 420 is comprised of a microcomputer and configured to control the overall operating conditions of the vehicle 500, such as the fuel supply from the fuel supply unit 410 to the internal combustion engine 400, the combustion state of the internal combustion engine 400 and the like, based on various operation parameters.

The fine particle sensor 100 is mounted to the exhaust pipe 415 of the internal combustion engine 400 and adapted to generate an output signal responsive to the amount of fine particles in the exhaust gas.

Figure 1B:
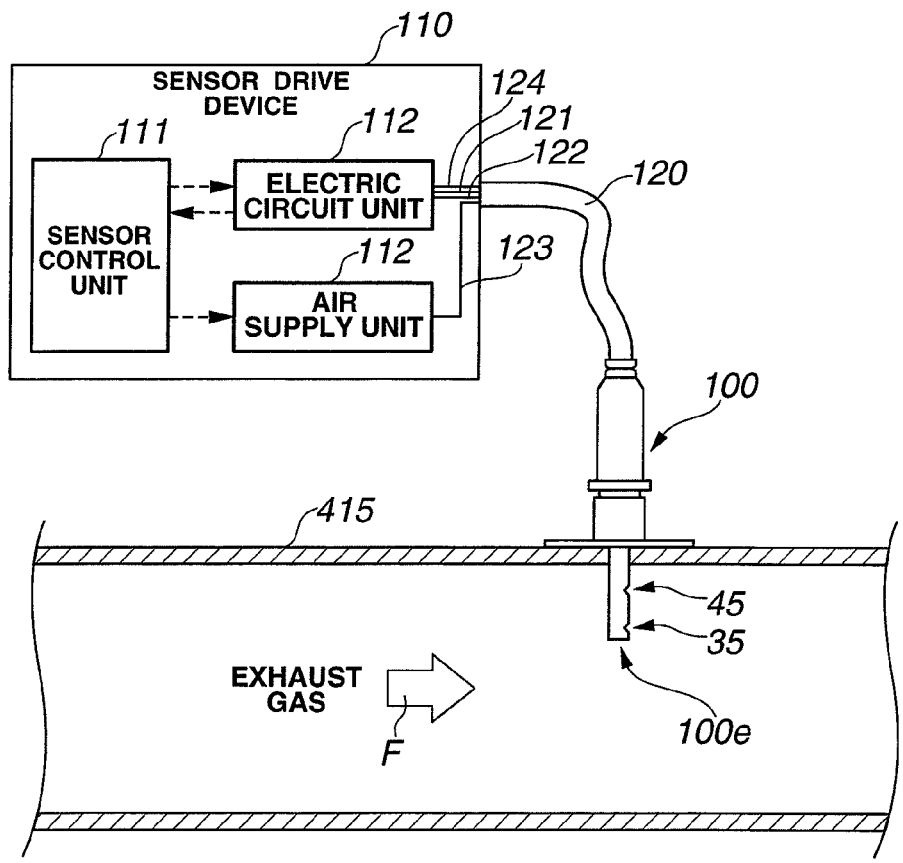

More specifically, the fine particle sensor 100 is fixed to an outer surface of the exhaust pipe 415 at a position downstream of the filter unit 416, with a straight rod-shaped front end portion (sensing portion) 100e of the fine particle sensor 100 inserted inside the exhaust pipe 415 and a flange portion 103f of the fine particle sensor 100 engaged on the outer surface of the exhaust pipe 415, as shown in FIG. 1B. In the present embodiment, the front end portion 100e of the fine particle sensor 100 is inserted so as to extend in a direction substantially perpendicular to the extension direction of the exhaust pipe 415 (i.e. the direction of flow of the exhaust gas in the exhaust pipe 415) at the mounting position of the fine particle sensor 100.

As will be explained in detail later, gas inlet and outlet holes 45 and 35 are formed in a casing CS of the front end portion 100e of the fine particle sensor 100 so that the exhaust gas flows in and out of the front end portion 100e of the fine particle sensor 100 through the gas inlet and outlet holes 45 and 35.

As the front end portion 100e of the fine particle sensor 100 is inserted in the exhaust pipe 415, there is no need to force the exhaust gas to branch off from and return to the exhaust pipe 415 for detection of the fine particles by the fine particle sensor 100. This leads to a downsizing of the fine particle detection system.

The sensor drive device 110 is connected to the fine particle sensor 100 through the cable 120 and configured to drive the fine particle sensor 100, determine the amount of fine particles in the exhaust gas according to an output signal of the fine particle sensor 100 and output the determination result to the vehicle control device 420. Herein, the amount of fine particles in the exhaust gas can be determined based on the surface area of the fine particles, the mass of the fine particles, the number of the fine particles or the like. The vehicle control device 420 may be configured to control the combustion state of the internal combustion engine 400 according to the determined fine particle amount and/or, when the determined fine particle amount is larger than a given level, inform a driver of the vehicle 500 of the occurrence of deterioration or defects in the filter unit 416.

Figure 5:
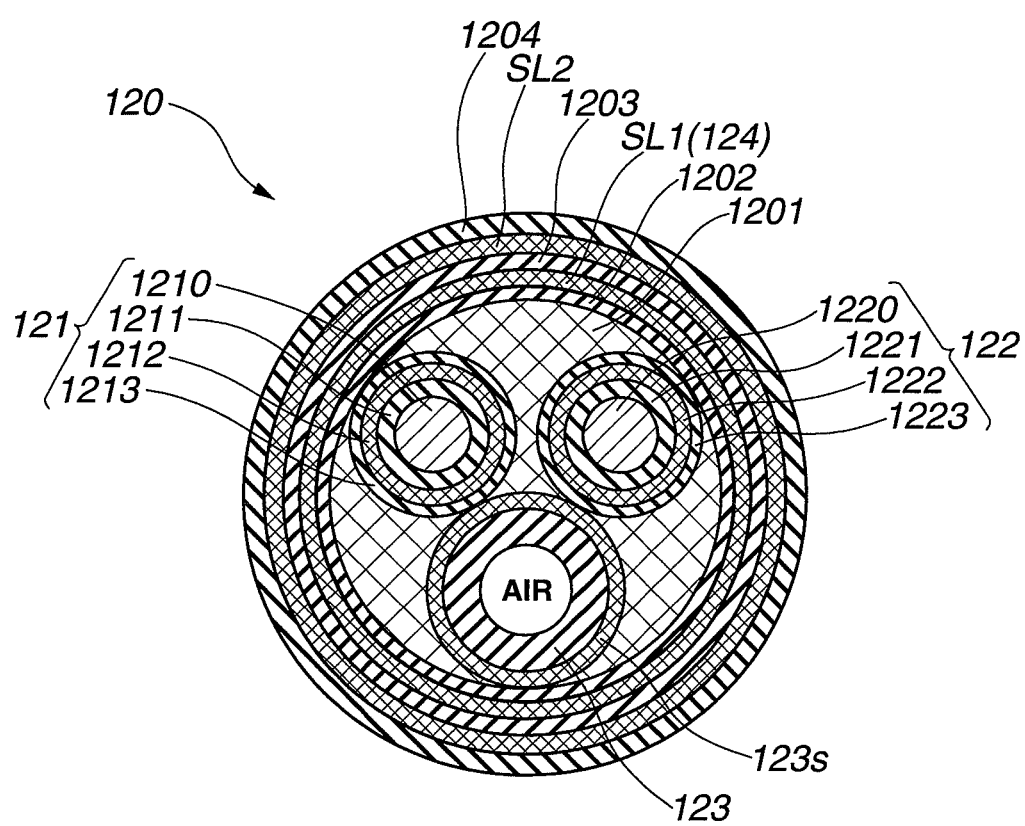
FIG. 5 is a section view of a cable for connecting a sensor drive device to the fine particle sensor according to the exemplary embodiment of the present invention.

As will be also explained in detail later, the cable 120 is a double-shield cable having a plurality of wiring/piping lines such as a first insulated wire 121, a second insulated wire 122, an air supply pipe 123, a first shield line SL1 (signal line 124) and a second shield line SL2 integrally accommodated in an outer sheath 1204 as shown in FIG. 5. This allows relatively free and easy wiring/piping line arrangement between the fine particle sensor 100 and the sensor drive device 110 so as to improve the ease of mounting the fine particle sensor 100 to the vehicle 500.

The structure of the fine particle detection system (the fine particle sensor 100, the cable 120 and the sensor drive device 110) will be now described below.

Figure 2:
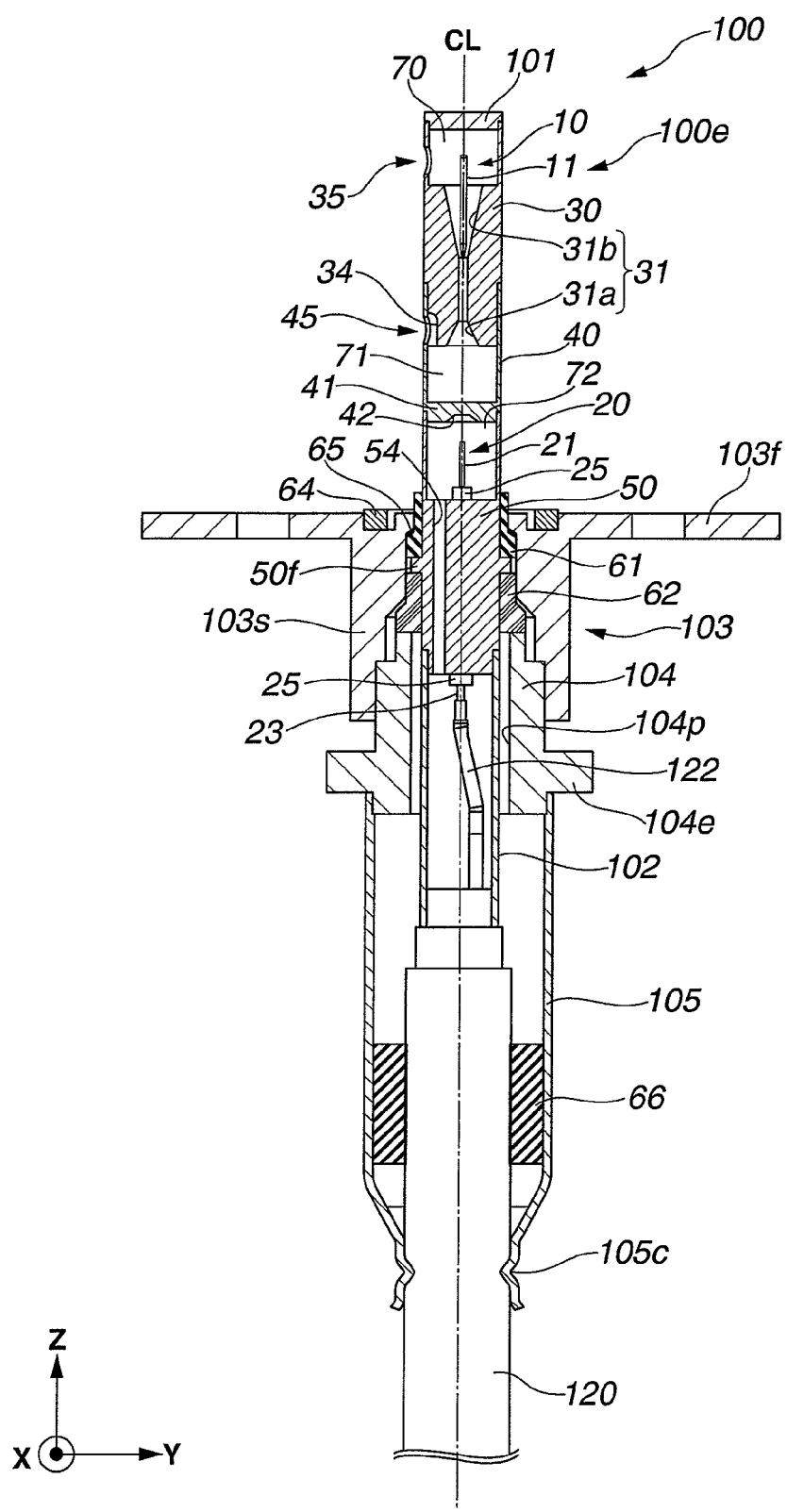
FIGS. 2 and 3 are schematic section views of the fine particle sensor, as viewed from different directions, according to the exemplary embodiment of the present invention.
Figure 3:
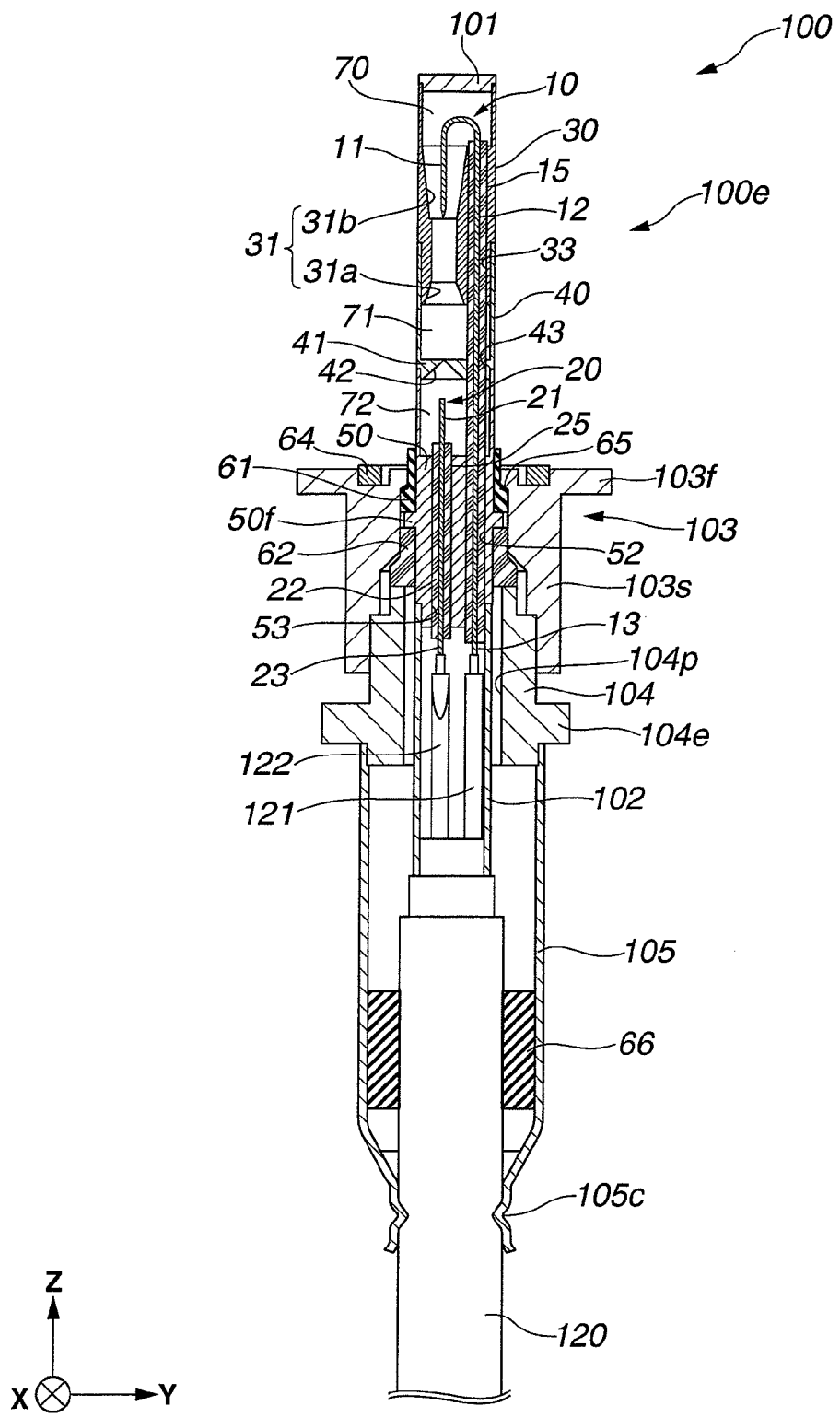
Figure 4:
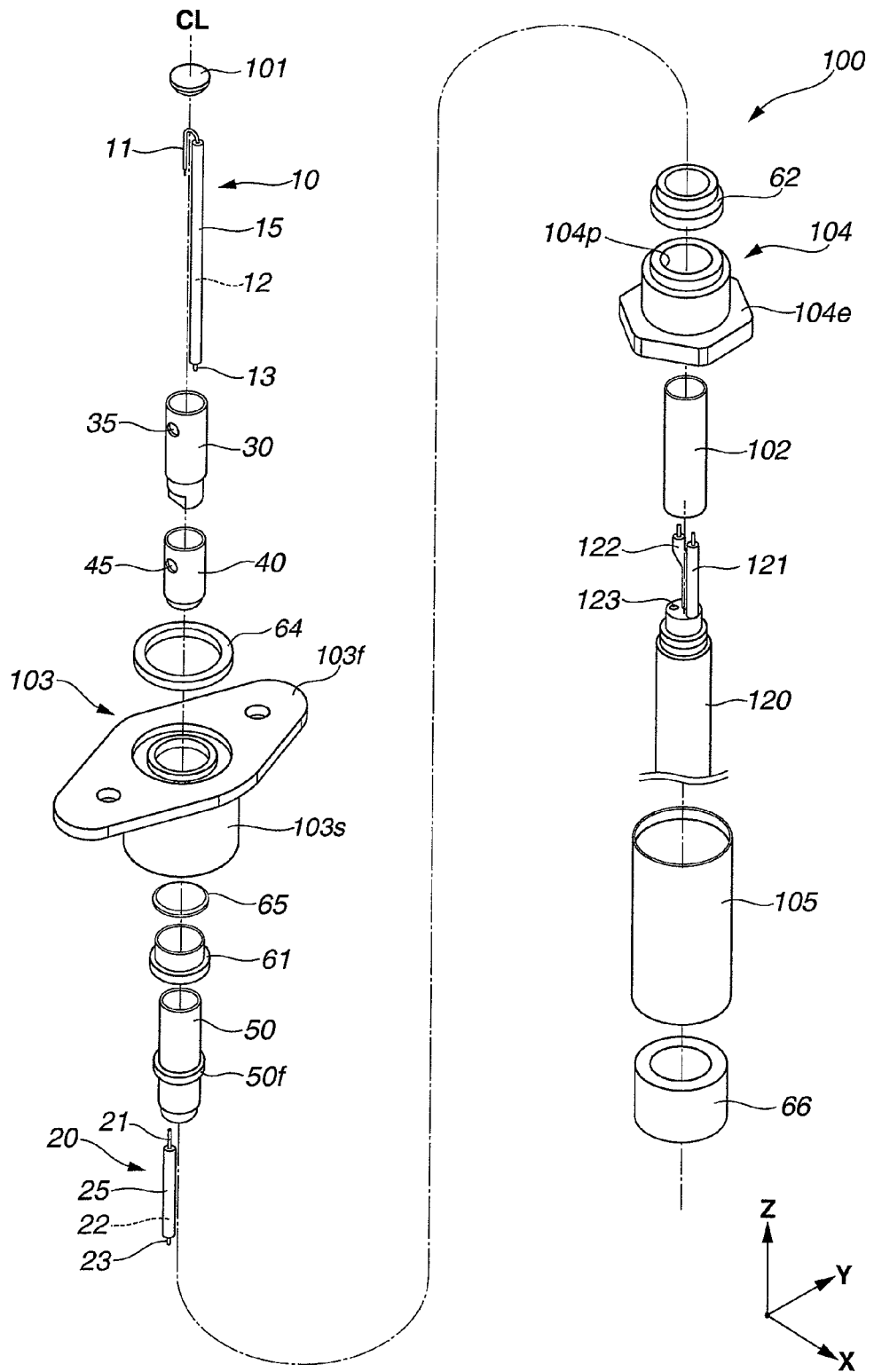
FIG. 4 is an exploded perspective view of the fine particle sensor according to the exemplary embodiment of the present invention.

As shown in FIGS. 2 to 4, the fine particle sensor 100 includes a first electrode member 10, a second electrode member 20, a mixing/discharging member 30, a nozzle member 40 and a holder member 50. It is noted that: the top and bottom sides in FIGS. 2 to 4 correspond to the front and rear sides of the fine particle sensor 100, respectively; and the three-dimensional X, Y and Z directions in FIGS. 2 to 4 refer to the lateral direction of the flange portion 103f, the longitudinal direction of the flange portion 103 and the axial direction CL of the fine particle sensor 100 (indicated by a dashed-dotted line), respectively.

The first electrode member 10 is substantially rod-shaped and has a body portion 12, a substantially U-shaped front end portion 11 located front of the body portion 12 and a rear end portion 13 located rear of the body portion 12. The body portion 12 of the first electrode member 10 is hermetically covered by a ceramic pipe 15. The ceramic pipe 15 is formed of insulating ceramic material such as alumina so that the first electrode 10 is kept insulated from the other conductive members by the ceramic pipe 15. Both of the front end and rear end portions 11 and 13 of the first electrode member 10 are exposed and protrude outside from the ceramic pipe 15. The rear end portion 13 of the first electrode member 10 is electrically connected with the first insulated wire 121 of the cable 120. Upon energization of the first electrode member 10 through the insulated wire 121, the front end portion 11 of the first electrode member 10 functions as an auxiliary electrode to assist in trapping ions as will be explained later.

The second electrode member 20 is rod-shaped throughout its length and has a body portion 22, a front end portion 21 located front of the body portion 22 and a rear end portion 23 located rear of the body portion 22. The body portion 22 of the second electrode member 20 is hermetically covered by a ceramic pipe 25. The ceramic pipe 25 is also formed of insulating ceramic material such as alumina so that the second electrode member 20 is kept insulated from the other conductive members by the ceramic pipe 25. Both of the front end and rear end portions 21 and 23 of the second electrode member 20 are exposed and protrude outside from the ceramic pipe 25. The rear end portion 23 of the second electrode member 20 is electrically connected with the second insulated wire 122 of the cable 120. Upon energization of the second electrode member 20 through the insulated wire 122, the front end portion 21 of the second electrode member 20 functions as a discharge electrode to generate ions by corona discharge as will be explained later.

Figure 6:
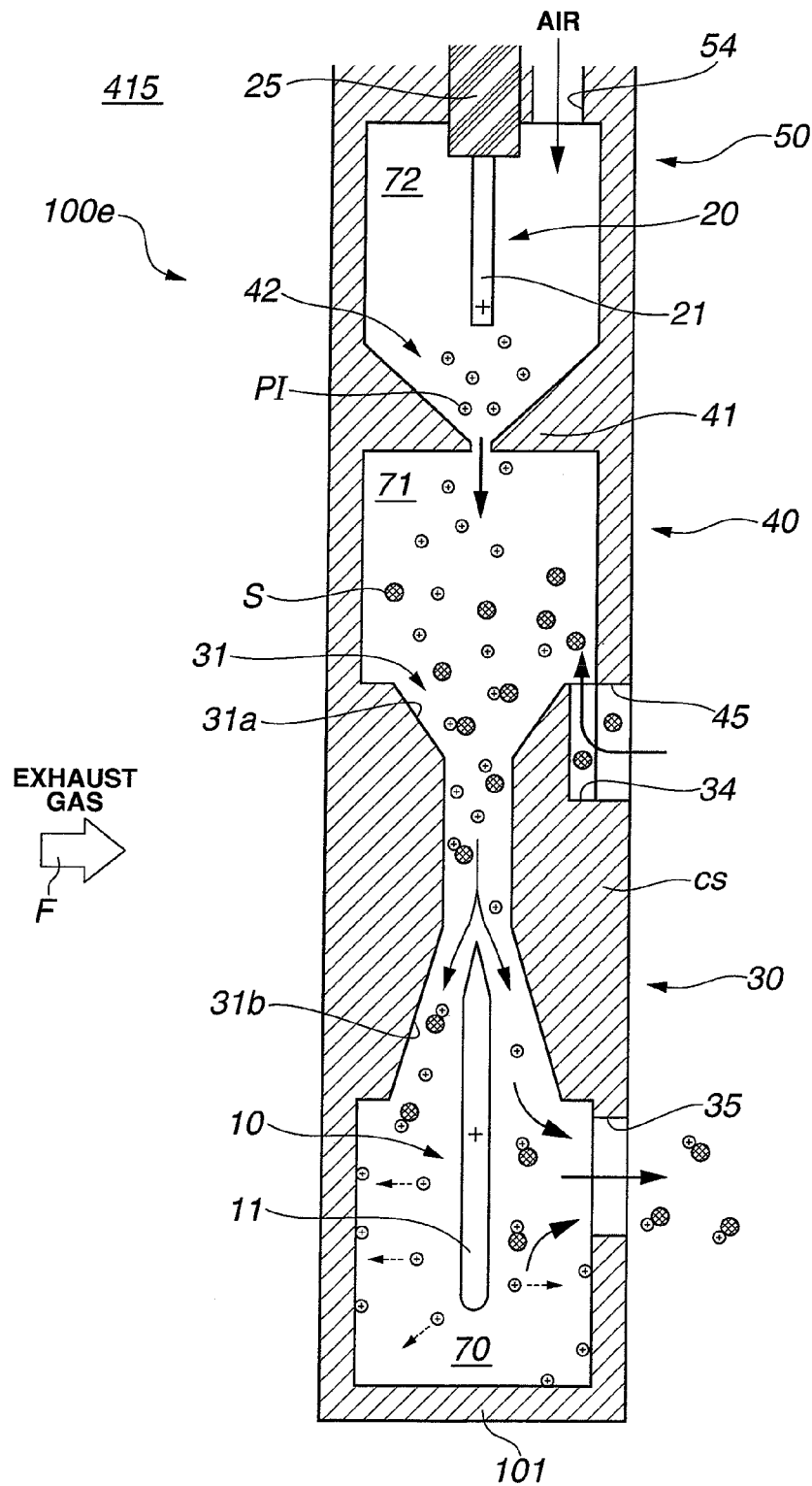
FIG. 6 is a schematic view showing the operations of the fine particle sensor according to the exemplary embodiment of the present invention.
Figure 7:
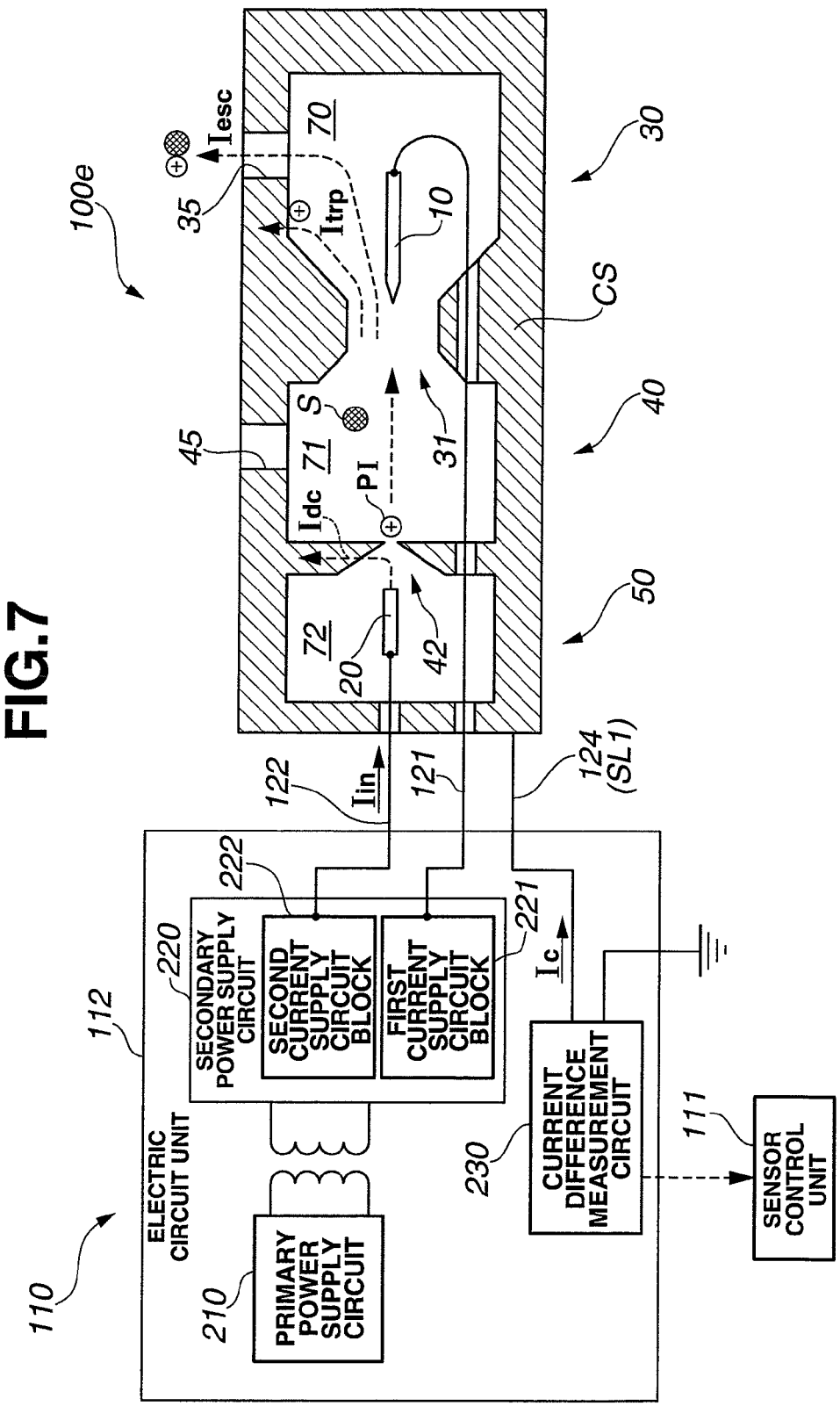
FIG. 7 is a schematic view showing the operations of the sensor drive device according to the exemplary embodiment of the present invention.

The mixing/discharging member 30, the nozzle member 40 and the holder member 50 are formed of conductive material, arranged adjacent to one another in a given arrangement direction (i.e. in the axial direction CL) in order of mention from the front side and joined together in series, with inner spaces 70, 71 and 72 of these structural members 30, 40 and 50 being in gas communication with one another. In the present embodiment, outer circumferential walls of the mixing/discharging member 30, the nozzle member 40 and the holder member 50 constitute the casing CS of the front end portion 100e of the fine particle sensor 100 as shown in FIGS. 6 and 7. Herein, the casing CS is in substantially cylindrical continuous form. (In FIGS. 6 and 7, the boundaries between the inner spaces 70, 71 and 72 of the mixing/discharging member 30, the nozzle member 40 and the holder member 50 are omitted whereby the casing CS is schematically illustrated as a single piece by the same hatching for the sake of simplicity.)

The mixing/discharging member 30 has a gas flow passage 31 and a pipe insertion hole 33 formed therethrough in parallel with each other in the axial direction CL (i.e. the Z direction in FIGS. 2 to 4). As shown in FIGS. 2 and 3, the gas flow passage 31 includes a first gas flow channel 31a communicating with the inner space 71 of the nozzle member 40 and a second gas flow channel 31b located front of (i.e. downstream of) the first gas flow channel 31 and communicating with the inner space 70 of the mixing/discharging member 30. The first gas flow channel 31a has an opening area decreasing toward the front (downstream side), whereas the second gas flow channel 31b has an opening area increasing toward the front (downstream side). The ceramic pipe 15 is hermetically fixed and retained in the pipe insertion hole 33 of the mixing/discharging member 30. In the mixing/discharging member 30, the front end portion 11 of the first electrode member 10 is bent at a position outside the pipe insertion hole 33 so as to extend from the inner space 70 into the second gas flow channel 31b substantially along the center of the second gas flow channel 31b. Further, a front end of the mixing/discharging member 30 is closed with a conductive cap 101.

The gas outlet hole 35 is formed in the outer circumferential wall of the mixing/discharging member 30 so as to provide communication between the inner space 71 of the mixing/discharging member 30 and the inside of the exhaust pipe 415.

The nozzle member 40 has, at a rear end thereof, a partition wall 41 between the inner space 71 of the nozzle member 40 and the inner space 72 of the holder member 50. A nozzle 42 is formed in the partition wall 41 as a communication hole between the inner space 71 of the nozzle member 40 and the inner space 72 of the holder member 50. In the present embodiment, the nozzle 42 is in the form of an orifice having an opening area decreasing toward the front (downstream side) so as to enable gas ejection toward the gas flow passage 31 of the mixing/discharging member 30. The nozzle member 40 also has a pipe insertion hole 43 so that the ceramic pipe 15 is hermetically fixed and retained in the pipe insertion hole 43 of the nozzle member 40.

The gas inlet hole 45 is formed in the outer circumferential wall of the nozzle member 40 so as to provide communication between the inner space 71 of the nozzle member 40 and the inside of the exhaust pipe 415.

Upon engagement of the mixing/discharging member 30 and the nozzle member 40, the gas flow passage 31 of the mixing/discharging member 30 is partly situated inside the nozzle member 40. The gas inlet hole 45 is thus formed at such a position as to overlap the gas flow passage 31 when the fine particle sensor 100 is viewed in an opening direction of the gas inlet hole 45 (that is, when the fine particle sensor 100 is viewed in a direction along the opening direction of the gas inlet hole 45 and perpendicular to the axial direction CL of the fine particle sensor 100). Further, a groove 34 is formed in the outer circumferential wall of the mixing/discharging member 30 in parallel with the gas flow passage 31 so that the gas inlet hole 45 is in communication with the inner space 71 of the nozzle member 40 through the groove 34 as shown in FIGS. 2 and 6.

The holder member 50 has an air supply hole 54 formed in a rear portion thereof in the axial direction CL (i.e. the Z direction in FIGS. 2 to 4) so as to provide communication between the inner space 72 of the holder member 50 and the air supply pipe 123 of the cable 120. The holder member 50 also has first and second pipe insertion holes 52 and 53 formed in parallel with the air supply hole 54 so that the ceramic pipes 15 and 25 are hermetically fixed and retained in the pipe insertion holes 52 and 53 of the holder member 50, respectively. In the holder member 50, the front end portion 21 of the second electrode member 20 is situated inside the inner space 72 with some gap for corona discharge left between the front end portion 21 of the second electrode member 20 and the partition wall 41 (nozzle 42). Further, a flange portion 50f is formed around the outer circumferential wall of the holder member 50.

A substantially cylindrical inner tube 102 is tightly fitted on a rear end portion of the holder member 50 and a front end portion of the cable 120. Within this inner tube 102, the rear end portions 13 and 23 of the first and second electrode member 10 and 20 protrude outside from a rear end of the holder member 50 and are electrically connected with exposed front end portions of the insulated wires 121 and 122 of the cable 120. The connections between the electrode 10 and the insulated wire 121 and between the electrode 20 and the insulated wire 122 can be thus protected by the inner tube 102.

In the present embodiment, the inner tube 102 is formed of conductive material and electrically connected to the first shield line SL of the cable 120 so as to function as a conduction pass between the front end portion 100e (structural members 30, 40 and 50) of the fine particle sensor 100 and the first shield line SL1 of the cable 120.

First and second annular insulative retaining members 61 and 62 are fixed around front and rear sides of the holder member 50 to hold therebetween the flange portion 50f of the holder member 50.

A fixing member 103 is attached around the retaining members 61 and 62 and has a substantially cylindrical body portion 103s, at a front end of which the flange portion 103f is formed for fixing the fine particle sensor 100 to the exhaust pipe 415. Steps are formed in an inner circumferential surface of the body portion 103s of the fixing member 102 and outer circumferential surfaces of the retaining members 61 and 62. The holder member 50 is thus fixed in position within the fixing member 103 by engagement of these steps in such a manner that the front end of the holder member 50 (the front end portion 21 of the second electrode member 20) protrudes toward the front from the flange portion 103f.

Herein, the fixing member 103 is formed of conductive material but kept insulated from the holder member 50 by the retaining members 61 and 62; and the first retaining member 61 has a portion protruding from a front end face of the flange portion 103f so that, when the fine particle sensor 100 is fixed to the exhaust pipe 415, the front end portion 100e of the fine particle sensor 100 is kept insulated from the exhaust pipe 415 by the protruding portion of the retaining member 61.

A ring-shaped gasket 64 is arranged in the flange portion 103f of the fixing member 30 so as to circumferentially surround the protruding front end of the holder member 50. Further, a plate packing 65 is arranged between the step of the outer circumferential surface of the first retaining member 61 and the step of the inner circumferential surface of the body portion 103s of the fixing member 103.

A joint 104 is screwed in a rear end of the cylindrical portion 103s of the fixing member 103 so as to hold the second retaining member 62 from the rear side. The joint 104 has a through hole 104p formed therein so that the rear end of the holder member 50 and the inner tube 102 are inserted in the through hole 104p. As there is some clearance left between an inner circumferential surface of the through hole 104p and outer circumferential surfaces of the holder member 50 and of the inner tube 102, the joint 104 and the holder member 50 are kept insulated from each other. The joint 104 also has a tool engagement portion 104e formed on an outer circumferential surface thereof for engagement with a mounting tool (e.g. hexagonal wrench).

A substantially cylindrical outer tube 105 is engaged in a rear end of the joint 104 so as to protect the joint between the inner tube 102 and the cable 120. An annular grommet 66 is arranged between the outer tube 105 and the cable 120 so as to protect the cable 120. A rear end of the outer tube 105 is crimped radially inwardly in such a manner that some part of the crimped rear end of the outer tube 105 becomes embedded into a cut of the outer sheath 1204 of the cable 120. With this, there is formed a crimped portion 105c that holds therein the cable 102 and provides electric conduction to the second shield line SL2 of the cable 120. (In FIG. 4, the rear end of the outer tube 105 before crimping is illustrated.)

As mentioned above and as shown in FIG. 5, the cable 120 has a structure that the first insulated wire 121, the second insulated wire 122, the air supply pipe 123, the first shield line SL1 (signal line 124) and the second shield line SL2 are integrally accommodated in the outer sheath 1204 for easy wiring/piping line arrangement between the fine particle sensor 100 and the sensor drive device 110 and for ease of mounting the fine particle sensor 100 to the vehicle 500.

The first insulated wire 121 has a core conductor 1210, a first resin coating layer 1211 formed around the core conductor 1210, a braided shield layer 1212 formed around the first resin coating layer 1211 and a second resin coating layer 1213 formed around the braided shield layer 1212.

Similarly, the second insulated wire 122 has a core conductor 1220, a first resin coating layer 1221 formed around the core conductor 1220, a braided shield layer 1222 formed around the first resin coating layer 1221 and a second resin coating layer 1223 formed around the braided shield layer 1222.

The first resin coating layer 1211 of the insulated wire 121, 122 is formed of fluororesin such as tetrafluoroethylene-hexafluoropropylene copolymer (FEP), whereas the second resin coating layer 1213 of the insulated wire 121, 122 is formed of fluororesin (such as FEP).

The air supply pipe 123 is formed into a hollow cylindrical shape of resin such as polytetrafluoroethylene (PTFE) and is covered with a reinforcing member 123s of e.g. braided metal.

A glass fiber part 1201 filled with a glass fiber is formed so as to cover and surround the first and second insulated wires 121 and 122 and the air supply pipe 123. A first resin coating layer 1202 is formed of resin such as PTFE between the glass fiber part 1201 and the first shield line SL1

The first shield line SL1 is formed of braided wire around the first resin coating layer 1202. A second resin coating layer 1203 is formed of resin around the first shield line SL1.

The second shield line SL2 is formed of braided wire around the second resin coating layer 1203.

Further, the outer sheath 1204 is formed of fluororesin such as FEP around the second shield line SL2.

In the above double-shield cable structure, the first shield line SL1 is electrically connected with the front end portion 100e (structural members 30, 40 and 50) of the fine particle sensor 100 as mentioned above so as to function as the signal line 124 between the front end portion 100e of the fine particle sensor 100 and the sensor drive device 110; and the second shield line SL2 is electrically connected with the crimped portion 105c of the outer tube 105 to make a connection to a ground through the outer tube 105, the joint 104, the fixing member 103, the exhaust pipe 415 and the chassis of the vehicle 500.

At the driving of the fine particle sensor 100, high-pressure air (compressed air) is supplied to the fine particle sensor 100 through the air supply pipe 123 of the cable 120. It is preferable that the pressure of the air supplied to the fine particle sensor 100 through the air supply pipe 123 is as high as possible for stable introduction of the exhaust gas into the fine particle sensor 100 as will be explained later. In other words, it is preferable that the air supply pipe 123 is adapted to supply higher-pressure air to the fine particle sensor 100. Further, it is preferable that the cable 120 has flexibility for free and easy wiring/piping line arrangement and for ease of mounting the fine particle sensor 100. In view of these circumstances, the air supply pipe 123 is preferably formed of resin so as to secure flexibility and pressure resistance.

In general, some region of the vehicle 500 in the vicinity of the exhaust pipe 415 reaches a high temperature (e.g. about 600° C.) during the operation of the internal combustion engine 400. As the cable 120 is partly arranged in such a high-temperature region of the vehicle 500, the pressure resistance of the resinous air supply pipe 123 may deteriorate due to temperature increase of the cable 120.

The reinforcing member 123s of lower thermoplasticity is thus formed around the air supply pipe 123 in the present embodiment. As the material of the reinforcing member 123s, there can suitably be used those having not only flexibility but also higher rigidity than the resin material of the air supply pipe 123. The braided metal is preferred as such a reinforcing material. Even if the resin material of the air supply pipe 123 becomes softened due to temperature increase, the air supply pipe 123 can be prevented from expansion deformation by the reinforcing member 123s. It is possible by the use of such a cable 120 to supply the higher-pressure air to the fine particle sensor 100 even under high-temperature conditions.

On the other hand, the sensor drive device 110 has a sensor control unit 111, an electric circuit unit 112 and an air supply unit 113 as shown in FIGS. 1B and 7. (In FIG. 7, the front end portion 100e of the fine particle sensor 100 and the sensor control unit 111 and the electric circuit unit 112 of the sensor drive device 100 are schematically illustrated.)

The sensor control unit 111 is comprised of a microcomputer and configured to operate the electric circuit unit 112 and the air supply unit 113 to drive the fine particle sensor 100, determine the amount of fine particles in the exhaust gas according to the output signal of the fine particle sensor 100 and output the determination result to the vehicle control device 420.

The electric circuit unit 120 is configured to supply electric power to the fine particle sensor 100 through the insulated wires 121 and 122 of the cable 120 and transmit the output signal of the fine particle sensor 100 to the sensor control unit 111 through the signal line 124 (first shield line SL1) of the cable 120.

As shown in FIG. 7, the electric circuit unit 112 has a primary power supply circuit 210, a secondary power supply circuit 220 and a current difference measurement circuit 230 in the present embodiment.

The primary power supply circuit 210 supplies high-voltage power to the secondary power supply circuit 220 through a transformer.

The secondary power supply circuit 220 includes a first current supply circuit block 221 connected to the first electrode member 10 through the first insulated wire 121 and a second current power supply circuit block 222 connected to the second electrode member 20 through the second insulated wire 122, to supply power from the first current supply circuit block 221 to the first electrode member 10 for ion trapping and supply power from the second current supply circuit block 222 to the second electrode 20 for corona discharge. In the present embodiment, the second current supply circuit block 222 is in the form of a constant-current circuit for supplying a constant current $I_{in}$ of the order of about 5 μA to the second electrode member 22 for corona discharge.

The current difference measurement section 230 measures the after-mentioned current difference value of the fine particle sensor 100 as the output signal through the signal line 124 (first shield line SL1) and transmits the sensor output signal to the sensor control unit 111.

Further, the air supply unit 113 is equipped with a pump to supply high-pressure air (compressed air) into the fine particle sensor 100 through the air supply line 123 of the cable 120. Any type of compressed gas other than high-pressure air (compressed air) can alternatively be supplied from the air supply unit 113 to the fine particle sensor 100.

In this way, the fine particle sensor 100 is mounted to the exhaust pipe 415 with the front end portion 100e of the fine particle sensor 100 inserted inside the exhaust pipe 415 and is connected the separately arranged sensor drive device 110 through the cable 120.

The operations of the above-structured fine particle detection system will be next explained below with reference to FIGS. 6 and 7. It is noted that: the portions, other than the front end portion 11, of the first electrode member 10 is omitted from FIG. 6 for the sake of simplicity; the direction of flow of the exhaust gas in the exhaust pipe 45 is indicated by arrow F in FIG. 6; and the direction of gas flow in the front end portion 100e of the fine particle sensor 100 and the direction of ion flow in the front end portion 100e of the fine particle sensor 100 are indicated by solid-line arrows and broken-line arrows, respectively, in FIGS. 6 and 7.

Under a command from the sensor control unit 111, the electric circuit unit 112 is operated to supply an input current $I_{in}$ from the second current supply circuit block 222 into the second electrode member 20 through the second insulated wire 122. By the supply of the input current $I_{in}$, there occurs corona discharge between the front end portion 21 of the second electrode member 20 (as a positive electrode) to the partition wall 41 of the nozzle member 40 (as a negative electrode) to thereby cause a discharge current $I_{dc}$ flowing from the second electrode member 20 to the casing CS through the partition wall 41 and generate positive ions PI (cations) in the inner space 72 of the holder member 50.

Further, the air supply unit 113 is operated to supply high-pressure air (compressed air) into the inner space 72 of the holder member 50 through the air supply pipe 123 and the air supply hole 54 under a command from the sensor control unit 111.

The generated positive ions PI are ejected, together with the high-pressure air, into the inner space 71 of the nozzle member 40 through the nozzle 42.

By the ejection of the high-pressure air through the nozzle 42, there can easily develop a negative pressure in the inner space 71 so that the exhaust gas containing soot S (as fine particles) acceleratedly flows from the exhaust pipe 415 into the inner space 71 through the gas inlet hole 45 under suction. As the flow of the exhaust gas into the inner space 71 is not affected by external factors such as the velocity of flow of the exhaust gas outside the fine particle sensor 100, a predetermined amount of exhaust gas can be stably and assuredly introduced into the inner space 71 through the gas inlet hole 45. This leads to an improvement of the detection accuracy of the fine particle sensor 100.

The higher the negative pressure caused by the ejection of the high-pressure air through the nozzle 42, the more favorably and acceleratedly the predetermined amount of exhaust gas flows into the inner space 71 through the gas inlet hole 45. It is thus preferable that the pressure of the air supplied to the fine particle sensor 100 is as high as possible in order to stably introduce the predetermined amount of exhaust gas into the inner space 71. In particular, the pressure of the air supplied to the fine particle sensor 100 is preferably set to a level that the ejection speed of the air through the nozzle 42 is as high as the speed of sound.

The exhaust gas introduced from the gas inlet hole 45 and the air ejected together with the positive ions PI from the nozzle 42 are mixed together in the inner space 71. If the soot S is present in the exhaust gas, some of the positive ions PI are adsorbed onto the soot S so that the soot S becomes positively charged with these ions PI.

As the gas inlet hole 45 is in communication with the inner space 71 through the groove 34, the direction of flow of the exhaust gas into the inner space 71 through the gas inlet hole 45 is opposite to the direction of ejection of the air into the inner space 71 through the nozzle 42 as shown in FIG. 2. As a result, there arises a larger turbulent flow in the inner space 71 so as to promote charging of the soot S by quick mixing of the air and the exhaust gas.

The exhaust gas mixed with the air flows from the inner space 71 into the inner space 70 of the mixing/discharging member 30 through the gas flow passage 31. As the opening area of the first gas flow channel 31a gradually decreases from the rear to the front (i.e. from the upstream side to the downstream side), it is possible by the first gas flow channel 31a to guide the flow of the gas smoothly to the downstream side and, at the same time, possible to stimulate collision of the positive ions PI with the soot S and thereby promote charging of the soot S.

At this time, the remainder of the positive ions PI remain as excess ions without being used for charging of the soot S (i.e. without being adsorbed onto the soot S).

The electric circuit unit 112 is operated to supply a current from the first current supply circuit block 221 into the first electrode member 10 through the first insulated wire 121 under a command from the sensor control unit 111. In the mixing/discharging member 30, the front end portion 11 of the first electrode member 10 extends from the second gas flow channel 31b to the inner space 70 along the direction of gas flow in the second gas flow channel 31b. A voltage is then applied between the front end portion 11 of the first electrode member 10 (as a positive electrode) and the circumferential walls of the second gas flow channel 31b and the inner space 70 (as a negative electrode) to thereby exert electrical repulsive force from the front end portion 11 of the first electrode 10 to the inner space 70.

Under such repulsive force, the excess ions PI are diverted outwardly by the first electrode member 10, and then, trapped by the circumferential walls of the second gas flow channel 31b and the inner space 70. As the opening area of the second gas flow channel 31b gradually increases from the rear to the front (i.e. from the upstream side to the downstream side), it is possible by the second gas flow channel 31b to efficiently divert the exhaust gas toward the wall surface of the inner space 70. Further, it is possible to allows inner surfaces of the circumferential walls of the second gas flow channel 31b and the inner space 70 (i.e., an inner surface of the circumferential wall of the casing CS) to function as a counter electrode to trap the excess ions PI. The efficiency of trapping of the excess ions PI can be thus improved by such a simple configuration. This also leads to an improvement of the detection accuracy of the fine particle sensor 100.

By contrast, the charged soot S is discharged together with the exhaust gas out from the inner space 70 to the exhaust pipe 415 through the gas outlet hole 35 because the influence of electric repulsive force or attractive force on the charged soot S is relatively small as the mass of the soot S is larger than that of the positive ion PI.

There accordingly occur a trap current $I_{trp}$ corresponding to the flow of the excess ions PI trapped by the casing CS and a leakage current $I_{esp}$ corresponding to the flow of the positive ions PI adsorbed onto the soot S and discharged to the outside of the casing CS.

In the present embodiment, the inner space 72 of the holder member 50, the front end portion 21 of the second electrode member 20 and the partition wall (nozzle forming component) 41 of the nozzle member 40 constitute an ion generating unit; the inner space 71 of the nozzle member 40 and the gas flow channel 31a of the mixing/discharging member 30 constitute a charging unit; and the front end portion 11 of the first electrode member 10 and the gas flow channel 31b and the inner space 70 of the mixing/discharging member 30 constitute an ion trapping unit as mentioned above.

Herein, the front end portion 100e of the fine particle sensor 100 is regarded as a closed circuit having a reference potential different from a reference potential of the vehicle 500 (also called "chassis ground") as the front end portion 100e of the fine particle sensor 100 is inserted in the exhaust pipe 45 in a state of being insulated from the exhaust pipe 415 and the chassis of the vehicle 500.

In such a closed circuit, the following equation (1) holds between the input current $I_{in}$, the discharge current $I_{dc}$, the trap current $I_{trp}$ and the leakage current $I_{esp}$.

$$I_{in}=I_{dc}+I_{trp}+I_{esp} \tag{1}$$

As mentioned above, the input current $I_{in}$ is kept constant by the constant-current supply circuit block 222; and each of the discharge current $I_{dc}$ and the trap current $I_{trp}$ is a flow of electricity through the casing CS. Namely, the leakage current $I_{esp}$ is determined by subtracting, from the constant input current $I_{in}$, the sum of these two currents $I_{dc}$ and $I_{trp}$ flowing through the casing CS according to the following equation (2).

$$I_{esp}=I_{in}-(I_{dc}+I_{trp}) \tag{2}$$

The intensity of the leakage current $I_{esp}$ corresponds to the amount of the positive ions PI used for charging of the soot S and depends on the amount of the soot S in the exhaust gas. The leakage current $I_{esp}$ can be thus read as the output signal of the fine particle sensor 100.

As mentioned above, the current difference measurement section 230 is electrically connected to the casing CS through the signal line 124 (first shield line SL1) of the cable 120 and is electrically grounded through the exhaust pipe 415 or the chassis of the vehicle 500 in the present embodiment. The reference potential of the casing CS is lower than the external reference potential as the total current flowing through the casing CS (i.e., the sum of the discharge current $I_{dc}$ and the trap current $I_{trp}$) is smaller by the leakage current $I_{esp}$ relative to the input current $I_{in}$. The current difference measurement section 230 supplies a compensation current $I_c$ to the casing CS through the signal line 124 so as to compensate such a potential difference. As this compensation current $I_c$ corresponds in value to the leakage current $I_{esp}$, the measurement section 230 measures the compensation current $I_c$ as a measurement value of the leakage current $I_{esp}$ and outputs the measurement result as the sensor output signal to the sensor control unit 111.

The sensor control unit 111 then determines the amount of the soot S in the exhaust gas based on the current output signal $I_{esp}$ with reference to a previously stored map or equation.

As described above, the amount of the soot S in the exhaust gas can be determined based on the change of electric current in the casing CS of the fine particle sensor 100 in the fine particle detection system.

By the way, the flow of the exhaust gas in the exhaust pipe 415 varies depending on the combustion state of the internal combustion engine 400. There is a possibility that the detection accuracy of the fine particle sensor 100 becomes unstable when the amount of flow of the exhaust gas into the fine particle sensor 100 changes with the velocity and rate of flow of the exhaust gas in the exhaust pipe 415.

In the present embodiment, the arrangement of the gas inlet and outlet holes 45 and 35 in the fine particle sensor 100 and the structure of mounting the fine particle sensor 100 to the exhaust pipe 415 are designed as follows in order to prevent the detection accuracy of the fine particle sensor 100 from deteriorating due to variations of the flow of the exhaust gas in the exhaust pipe 415.

As shown in FIG. 8A, the gas inlet and outlet holes 45 and 35 are arranged in such a manner as to overlap each other when the fine particle sensor 100 is viewed in an extension direction of the front end portion 100e of the fine particle sensor 100 (i.e. in a direction of arrangement of the charging unit and the ion trapping unit) as indicated by arrow P. The gas inlet and outlet holes 45 and 35 do not necessarily completely overlap each other and may partially overlap each other when viewed in the extension direction of the front end portion 100e of the fine particle sensor 100. For example, it is feasible that the gas inlet and outlet holes 45 and 35 can be offset from each other in a circumferential direction of the front end portion 100e of the fine particle sensor 100 as shown in FIG. 8B. (In FIGS. 8A and 8B, the formation width of the gas outlet hole 35 are indicated by broken lines for the purpose of showing the overlap position between the gas inlet and outlet holes 45 and 35.)

In this gas inlet/outlet hole arrangement, the gas inlet and outlet holes 45 and 35 are subjected to substantially the same pressure from the flow of the exhaust gas in the exhaust pipe 415. Thus, the influence of the flow of the exhaust gas in the exhaust pipe 415 on the amount of the exhaust gas flowing into the gas inlet hole 45 is substantially the same as the influence of the flow of the exhaust gas in the exhaust pipe 415 on the amount of the exhaust gas flowing out of the gas outlet hole 35. It is therefore possible to reduce the influence of variations of the flow of the exhaust gas in the exhaust pipe 415, stabilize the amounts of the exhaust gas flowing in and out of the front end portion 100e of the fine particle sensor 100 and secure the stable detection accuracy of the fine particle sensor 100.

As shown in FIG. 8A or 8B, the gas inlet and outlet holes 45 and 35 are of the same size in the present embodiment. However, the gas inlet and outlet holes 45 and 35 can alternatively be of different sizes as long as the gas inlet and outlet holes 45 and 35 are arranged so as to at least partially overlap each other when viewed in the extension direction of the front end portion 100e of the fine particle sensor 100.

Moreover, the fine particle sensor 100 is mounted to the exhaust pipe 415 in such a manner that openings of the gas inlet and outlet holes 45 and 35 are directed downstream of the flow of the exhaust gas in the exhaust pipe 415 as shown in FIG. 8C. (In FIG. 8C, the gas inlet and outlet holes 45 and 35 are indicated by broken line; the direction of opening of the gas inlet/outlet hole 45, 35 is indicated by arrow OD; and the direction of flow of the exhaust gas in the exhaust pipe 45 is indicated by arrow F.)

In this sensor mounting structure, the front end portion 100e of the fine particle sensor 100 receives the flow of the exhaust gas at a side opposite from the gas inlet and outlet holes 45 and 35 so that the flow of the exhaust gas in the vicinities of the gas inlet and outlet holes 45 and 35 becomes relatively gentle. It is therefore possible to reduce the influence of variations of the flow of the exhaust gas in the exhaust pipe 415, stabilize the amounts of the exhaust gas flowing in and out of the front end portion 100e of the fine particle sensor 100 and secure the detection accuracy of the fine particle sensor 100. It is also possible to, in the occurrence of liquid drops of condensed water etc. in the exhaust pipe 415, prevent such liquid drops from getting into the casing CS of the front end portion 100e of the fine particle sensor 100 through the gas inlet and outlet holes 45 and 35 under the flow of the exhaust gas.

The opening direction OD of the gas inlet/outlet hole 45, 35 is not necessarily in parallel with the direction of flow of the exhaust gas in the exhaust pipe 415. As long as the opening direction OD of the gas inlet/outlet hole 45, 35 is a downstream direction of the exhaust pipe 415, the opening direction OD of the gas inlet/outlet hole 45, 35 may be e.g. at an angle of 45° or less with respect to the direction of flow of the exhaust gas in the exhaust pipe 415.

As described above, the fine particle sensor 100 of the present embodiment is able to detect the amount of the fine particles such as soot S in the exhaust gas of the internal combustion engine 400 by the simple and compact configuration. In the above gas inlet/outlet hole arrangement and sensor mounting structure, the flow of the exhaust gas into and out of the fine particle sensor 100 can be stabilized for improvement of the detection accuracy of the fine particle sensor 100. Further, the air supply pipe 23 is covered with the reinforcing member 123s in the cable 120 so that the fine particle sensor 100 can be supplied with higher-pressure air through the air supply pipe 23 for further improvement in detection accuracy.

The entire contents of Japanese Patent Application No. 2011-058627 (filed on Mar. 17, 2011) are herein incorporated by reference.

Although the present invention has been described above with reference to the specific exemplary embodiment, the present invention is not limited to the above-described exemplary embodiment. Various modifications and variations of the embodiment described above will occur to those skilled in the art in light of the above teachings. For example, the following modifications are possible.

First Modification

The ion generating unit, the charging unit and the ion trapping unit are arranged in the front end portion 100e of the fine particle sensor 100 in the above embodiment. The ion generating unit is not however necessarily arranged in the front end portion 100e of the fine particle sensor 100. At least the charging unit and the ion trapping unit can be arranged in the front end portion 100e of the fine particle sensor 100. That is, it is not necessary to accommodate the ion generating unit in the casing CS as long as at least the charging unit and the ion trapping unit are accommodated in the casing CS. In this case, the ion generating unit may be arranged in the fine particle sensor 100 at a position outside the exhaust pipe 415 and separate from the charging unit and the ion trapping unit.

Second Modification

The nozzle 42 is not necessarily formed in the partition wall 41 as a communication hole between the inner space 72 of the holder member 50 and the inner space 71 of the nozzle member 40 although the nozzle 42 is formed between these two inner spaces 72 and 71 in the above embodiment. However, there develops a negative pressure in the inner space 71 by the ejection of the air into the inner space 71 through the nozzle 42 so that the exhaust gas can be favorably introduced from the exhaust pipe 415 into the inner space 71 through the gas inlet hole 45 under suction as mentioned above. The formation of the nozzle 42 between the inner spaces 72 and 71 is thus effective to stabilize the amount of the exhaust gas introduced into the fine particle sensor 100 and improve the detection accuracy of the fine particle sensor 100.

Third Modification

Although the front end portion 100e of the fine particle sensor 100 is inserted in the direction substantially perpendicular to the extension direction of the exhaust pipe 415 in the above embodiment, the direction of insertion of the front end portion 100e of the fine particle sensor 100 is not necessarily substantially perpendicular to the extension direction of the exhaust pipe 415 and may be inclined with respect to the extension direction of the exhaust pipe 415.

Fourth Modification

In the above embodiment, the air supply pipe 123 of the cable 120 is covered with the metal-braided reinforcing member 123s. The reinforcing member 123s may alternatively be formed of any other material having lower thermoplasticity than the resin material of the air supply line 123. It is feasible to compensate for a deterioration in the pressure resistance of the air supply pipe 123 caused by temperature increase of the cable 120 when the reinforcing member 123s is formed of low thermoplastic material.

Fifth Modification

Further, the reinforcing member 123s is provided to cover and surround the entire circumference of the air supply pipe 123 in the above embodiment. Alternatively, the reinforcing member 123s may be provided around only part of the air supply pipe 123 located e.g. in the vicinity of the fine particle sensor 100 or in the vicinity of the exhaust pipe 415.

Sixth Modification

Although the first and second insulated wires 121 and 122, the air supply pipe 123 etc. are incorporated in the cable 120 in the above embodiment, it suffices that the cable 120 incorporates therein at least the second insulated wire 122 connected to the second electrode member 20 (as a discharge electrode) and the air supply pipe 123 covered with the reinforcing member 123s.

Seventh Modification

In the above embodiment, the cable 120 has a double-shield structure formed by the shield lines SL1 and SL2 and utilizes the shield line SL1 as the signal line 124 between the front end portion 100e of the fine particle sensor 100 and the electric circuit unit 112. The shield line SL is not however necessarily provided in the cable 120. The signal line 124 may be provided separately from the shield line SL1 and may not be incorporated in the cable 120.

Eighth Modification

The sensor control unit 111 can be configured to determine the amount of the soot S in the exhaust gas based on any parameter according to the amount of the ions PI trapped by the ion trapping unit of the fine particle sensor 100 although the sensor control unit 111 retrieves the compensation current $I_c$, which corresponds to the leakage current $I_{esc}$, from the current difference measurement section 230 and determines the amount of the soot S in the exhaust gas according to the retrieved compensation current $I_c$ in the above embodiment. For example, it is alternatively feasible to measure a potential of the casing CS lowered according to the amount of the ions PI trapped by the ion trapping unit, and then, determine the amount of the soot S in the exhaust gas based on the measured potential of the casing CS.

Ninth Modification

In the above embodiment, the inner circumferential wall surface of the casing CS is used as the negative electrode for corona discharge and for ion trapping. Alternatively, a negative electrode may be provided as a separate structural component from the casing CS.

Tenth Modification

The fine particle sensor 100 is so structured as to generate positive ions PI by corona discharge between the second electrode member 20 and the partition wall (nozzle forming member) 41 and allow the first electrode member 10 to exert electrical repulsive force on the positive ions PI in the above embodiment. The structure of the fine particle sensor 100 is not however limited to the above. In the fine particle sensor 100, the positive/negative connections of the first and second electrode members 10 and 20 and the partition wall 41 may be changed so as to generate negative ions by corona discharge between the second electrode member 20 and the partition wall 41 and allow the first electrode member 10 to exert electrical repulsive force on the negative ions.

The scope of the invention is defined with reference to the following claims.

What is claimed is:

1. A fine particle sensor for detecting fine particles in exhaust gas flowing through an exhaust pipe of an internal combustion engine, comprising:
    an ion generating unit that generates ions by corona discharge;
    a charging unit that charges, with some of the ions generated by the ion generating unit, the fine particles in the exhaust gas emitted from the internal combustion engine through the exhaust pipe;
    an ion trapping unit that traps a remainder of the ions generated by the ion generating unit, which remain as excess ions without being used for charging of the fine particles in the charging unit, so that the fine particle sensor can generate an output signal responsive to the amount of the fine particles in the exhaust gas according to the amount of the excess ions trapped by the ion trapping unit; and
    a casing inserted inside the exhaust pipe and accommodating therein the charging unit and the ion trapping unit adjacent to each other in a given arrangement direction, the casing having, formed in a circumferential wall thereof, a gas inlet hole for introducing the exhaust gas from the exhaust pipe into the charging unit and a gas outlet hole for discharging the exhaust gas that includes the fine particles charged with the some of the ions generated by the ion generating unit, out from the ion trapping unit to the exhaust pipe,
    wherein the gas inlet and outlet holes are arranged in such a manner as to at least partially overlap each other when the fine particle sensor is viewed in the given arrangement direction.

2. The fine particle sensor according to claim 1, wherein the casing accommodates therein the ion generating unit adjacent to the charging unit and has a partition wall formed with a communication hole between the ion generating unit and the charging unit; and wherein the ion generating unit is externally supplied with gas and ejects the supplied gas together with the generated ions into the charging unit through the communication hole so that the exhaust gas flows from the exhaust pipe into the charging unit through the gas inlet hole under suction.

3. The fine particle sensor according to claim 1, wherein the casing defines therein a gas flow passage through which the exhaust gas flows together with the charged fine particles and the excess ions from the particle charging unit to the ion trapping unit; and wherein the gas flow passage includes a first gas flow channel having an opening area decreasing toward a downstream side and a second gas flow channel formed downstream of the first gas flow channel and having an opening area increasing toward a downstream side.

4. The fine particle sensor according to claim 3, wherein the ion trapping unit has a rod-shaped auxiliary electrode extending to the gas flow passage so as to divert the excess ions outwardly thereof and a counter electrode formed around the auxiliary electrode by an inner surface of the circumferential wall of the casing so as to trap the excess ions.

5. A mounting structure for mounting the fine particle sensor according to claim 1 to an exhaust pipe of an internal combustion engine, wherein the fine particle sensor is arranged in such a manner that openings of the gas inlet and outlet holes are directed downstream of the flow of exhaust gas in the exhaust pipe.

* * * * *